United States Patent [19]

Light

[11] Patent Number: 5,213,553
[45] Date of Patent: May 25, 1993

[54] DEVICES USED TO IMPROVE SPEECH, SWALLOWING AND MASTICATION

[76] Inventor: Jack Light, 104 New Mark Esplanade, Rockville, Md. 20850

[21] Appl. No.: 868,343

[22] Filed: Apr. 15, 1992

[51] Int. Cl.$^5$ .......................................... A63B 23/025
[52] U.S. Cl. ....................................... 482/11; 128/12; 128/15; 128/777; 434/185
[58] Field of Search .................... 482/11; 128/12, 777, 128/15, 67, 860, 861, 859; 434/185; 84/466

[56] References Cited

U.S. PATENT DOCUMENTS

| | | | |
|---|---|---|---|
| 779,360 | 1/1905 | Grummann | 84/466 |
| 3,014,286 | 12/1961 | Hricak | 84/466 |
| 3,286,576 | 11/1966 | West . | |
| 3,738,477 | 10/1973 | Anders et al. | 128/15 |
| 3,744,485 | 7/1973 | Worthy . | |
| 3,867,770 | 2/1975 | Davis | 434/185 |
| 4,718,662 | 1/1988 | North . | |
| 4,862,903 | 9/1989 | Campbell . | |
| 4,986,283 | 1/1991 | Tepper . | |
| 4,997,182 | 5/1991 | Kussick | 482/11 |

*Primary Examiner*—Richard J. Apley
*Assistant Examiner*—Lynne Reichard
*Attorney, Agent, or Firm*—J. Gibson Semmes

[57] ABSTRACT

A complemental series of handheld, tactile devices in kit form to assist in behavioral modification training techniques as well as utilizing the techiques of "resisted movement" and "successive approximation". Each positioner device is handheld, with one portion protruding from the lips and the other portion loosely fitting on the patient's hard plate. Different shapes are introduced to the tongue and lips on each respective device. A commonalty within the interdependent positioner devices is presented by an elongated palatal base defining a convex upper surface to engage the palate, a manipulable handle projecting from the base and the respective devices are further characterized in configuration. Variations in configuration such as elongation, thickenings and apertures of the positioners involve primary modification to the palatal base and adjacent interconnection of the handle, whereby upon activation the patient may exercise his tongue and lips to achieve consonantal speech sounds, perfect swallowing techniques, and aid in mastication.

5 Claims, 3 Drawing Sheets

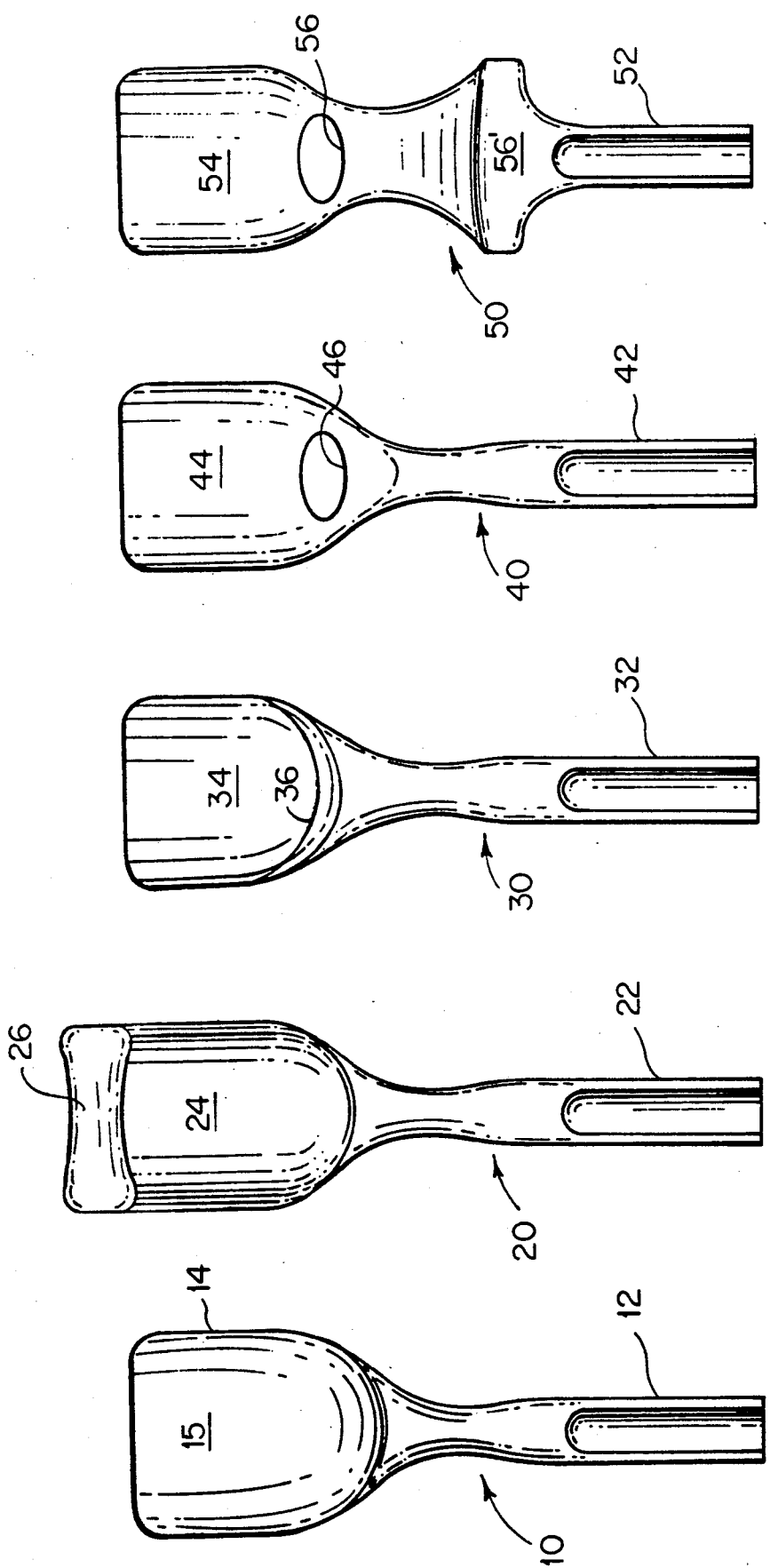

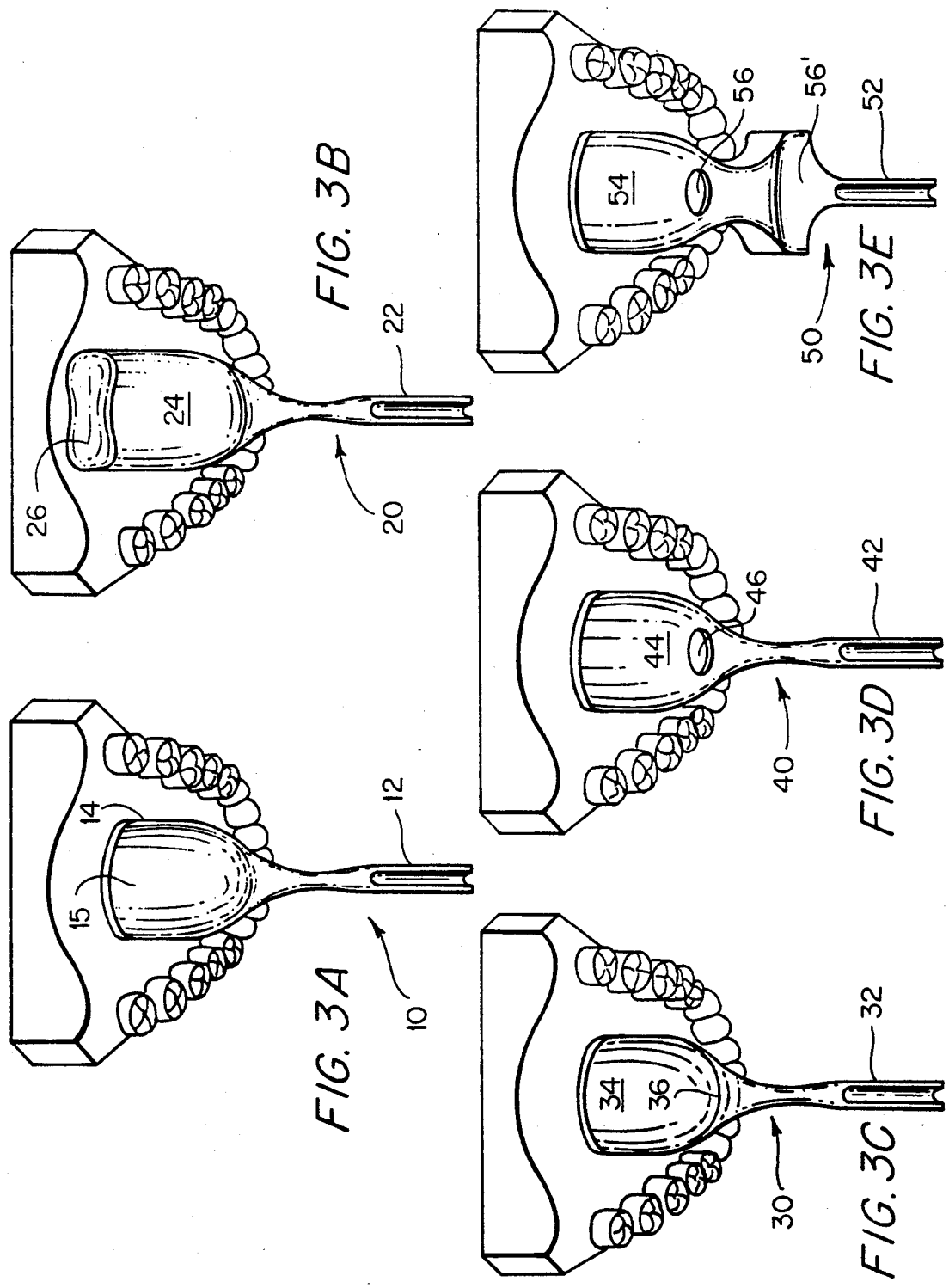

DEVICES USED TO IMPROVE SPEECH, SWALLOWING AND MASTICATION

BACKGROUND OF THE INVENTION

In the normal function of speech production, mastication and swallowing, the functioning tissues of the oral cavity consist of mobile and nonmobile structures. Mobile structural elements include the tongue, cheeks, lips and the soft palate, whereas the nonmobile elements are the hard palate, mandible and teeth. The structures interact in specific combinations to produce speech, swallowing and mastication. For example, to initiate and execute a swallow, the teeth are brought together, lips are closed, intraoral pressure is built up, the anterior portion of the tongue presses against the anterior portion of the hard palate, and the tongue dorsum rolls posteriorly over the palate, which forces saliva or a food bolus into the pharynx. For speech articulation, precise contacts are needed whereby consonantal sounds are produced by touching the palate with the tongue in very specific accurate contact areas, and vowels by permitting varying air streams to flow. For mastication of food, all of the oral musculature are brought into play, viz.: the tongue, lips and cheeks aid in carrying the food bolus to the teeth, a food table, and in preventing the food from dispersing during trituration.

The tongue, being the major articulator of the oral structures, must adjust for each speech sound. The tip, the edges and the base thereof must move some times as fast as thirty times per second, and each movement must hit the target, hard palate and teeth, at which it is aimed, with extraordinary accuracy. If it misses by even a fraction of an inch, the wrong sound will be produced.

A mature speaker relies heavily for this performance on touch, sense of cutaneous pressure, and kinesthesis, awareness of position and movement of the speech mechanism. The reliance includes more than sensations of touch and kinesthesis, it includes the neural process by which one perceives his body in relation to objects and space. It is this perceptual system by which we are literally in touch with our environment. The "feel" of speech is thus vital for normal performance, and plays a role in the speech transmitter system.

The speech transmitter system has at least two roles. It has an afferent role in transmitting the code of nerve impulses generated by the speech receptors to central parts of the speech system. The system also has an efferent role in transmitting patterns of motor impulses from the central speech system to the peripherial speech effector system. The tactile-kinesthetic transmitter system is utilized in speech control and monitoring function. If these speech receptors are not receiving and converting stimulation into codes of nerve impulses, there is dysfunction of the transmission system and reduced significant impulses of the central speech regions. As a result, there occurs a reduction in transmission of the motor impulses that have been organized in higher centers. Thus, decreased sensory input leads to decreased motor output which results in inaccurate production of speech. Equally, sensory and motor controls are involved in the feeding and swallowing mechanisms.

An abnormal oral environment may show impairment due to abnormality of the nonmobile and or mobile elements. Whereas the palate, mandible or teeth are nonmobile, they may be amenable to correction or reconstruction by surgical and or prosthetic intervention, such as is not within the purview of the present invention. Abnormalities of the mobile features of the oral environment may be the result of structural deficiency, such as a cleft palate, other congenital anomaly or cancer surgery of the tongue as an acquired defect. Functional impairment also may be congenital, developmental or acquired. Development of abnormal muscle patterns leading to oral and facial imbalances is present in "tongue thrusting". Acquired neurological functional abnormalities are due to stroke and head injuries. When there are disturbances of the neurogenic motor controls for speech, individuals will experience difficulty with strength, range of motion and or coordination of movements of the tongue, lips and soft palate, resulting in unintelligible speech and or swallowing. Individuals experiencing these difficulties are named "dysarthric", their speech may sound slurred, dysrythmic or hypernasal.

Current speech pathology intervention, that is speech therapy, aims at improving strength, range of motion and coordination of speech musculature. One known method of improving the strength of contact, the range of motion and the accuracy of the tongue and lips is called the "resisted movement" technique. For example, if the individual has difficulty in raising the anterior part of the tongue, the clinician applies graded pressure in a downward direction to the tongue while requesting the individual to attempt to lift his tongue against this resistance. The procedure may succeed in increasing or triggering additional muscular activity and the tongue tip may show increased movement upwards. Three or four maneuvers by the clinician should precede each request for the patient to raise the tongue without the presence of the downward pressure. The device generally available and used is a tongue depressor. Such training requires individual sessions between patient and speech therapist. One objective of such tongue exercises is to improve the strength, range of motion and accuracy of the tongue-palate contacts for speech and swallowing. The available capacity must be directed into specific neuromuscular patterns to achieve different maximal accuracy. This is accomplished by helping the patient through a process of "successive approximations" until accurate tongue-palate contacts are made.

A second possible approach is the placement of a prosthesis which provides palatal augmentation to compensate for tongue movement dysfunction. These prostheses must be designed individually to fit the patient and the use of such prostheses is limited by several factors: First, the patient's teeth must be suitable to support a prosthesis properly; a maxillofacial prosthodontist is needed to design, produce and fit the device; and finally, the cost must be considered.

SUMMARY OF INVENTION

The present invention consists of a new approach to rehabilitation of dysarthric and other orally dysfunctional persons, a complemental series of handheld, tactile devices assist in "resisted-movement" training techniques as well as in behavioral modification training, utilizing the process of "successive approximation". The devices are all handheld with one portion protruding from the lips and the other portion loosely fitting on the hard palate. Different shapes are introduced to the tongue and lips on complemental devices. These devices are a series interdependent to accomplish a particular task of exercising the tongue and lips towards a goal, so that the tongue and lips will be strengthened to make the series of accurate contact for speech sounds or be exercised for the range of motion involved in swallowing. The contours contact with the tongue and lips, also acting as exercisers due to the resistant movement techniques herein.

In conducting the exercises possible with the various shaped devices heretofore proposed, the following instrumentation is utilized, coactively by a speech language pathologist and other members of a rehabilitation team in treating patients for speech therapy and or oral rehabilitation of structurally and functionally impaired individuals having a degree of dysfunction, requiring speech and or swallowing improvement.

Among the advantages achieved through the adoption, usage and distribution of the coactive devices are the following: Not only are the devices non-invasive, they are likewise non-toxic and suitable for cold sterilization. They are susceptible of mass production and, accordingly, inexpensive as compared to related prostheses. It is significant that the dental condition of the patient's mouth is not a limiting factor; moreover, the stroke patient's reduced motor control and mental monitoring skills are no barrier to improvement since the devices will provide training and conditioning without such abilities. In this connection, the devices facilitate achieving specific muscle movement patterns which are otherwise difficult to achieve with current resisted-movement techniques.

Patients undergoing treatment with these devices do not require specialist services by the maxillofacial prosthodontist. Additionally, speech therapists may readily select the appropriate devices herein, thus enhancing the introduction of the devices to the professions. In fact, patients may use the devices on their own following a selected protocol determined by their therapist, and since they are not restricted to therapy sessions, selected patients' use will accelerate their rehabilitation process.

It is accordingly an objective of invention to provide these interdependent devices to at least three patient groups as follows: the neurologically impaired, including stroke and head trauma patients, as well as persons with degenerative diseases; the functionally impaired, including tongue thrusters, and those having undergone laryngectomees who as a result comprise poor esophageal speakers Other potential users include cleft palate patients having abnormal tongue movements.

In addition, the devices comprising the kit yield, upon adaptation, to additional advantages over the known art, as follows:

(a) The devices of the kit are non-invasive, non-toxic, suitable for autoclaving, gas and cold sterilization. Their use is not dependent on the status of the patients teeth.

(b) Speech Language Pathologists do not have to accept a new concept of speech therapy, but will find an aid for supporting "resisted movement" and "successive approximation" techniques, since the devices help achieve the muscle movement patterns utilized in these exercises. The selection of the appropriate devices for specific patients is no problem, since the Speech Language Pathologist is aware of what consonants require remediation; moreover, the protocols for the exercises are extremely simple to administer.

(c) Patients have no difficulty in using the devices and exhibit no reluctance to use them. Patients' reduced motor skills and cognitive status play less of a role in using the devices.

DESCRIPTION OF DRAWINGS

FIGS. 1A, 1B, 1C, 1D and 1E are plan views of the respective handheld positioner devices wherein the tongue contacting portions of the palatal base elements are exposed at the top half of each drawing.

FIGS. 3A, 3B, 3C, 3D and 3E are perspective views of the respective positioner devices comprising the kit depicted in FIGS. 1A-E and 2A-E aforesaid, the devices each being shown in placement on a model of the human hard palate.

DESCRIPTION OF THE PREFERRED EMBODIMENTS

In lieu of a fixed artificial palatal prosthesis, handheld tactile aides were developed to assist with "resisted movement" as well as with "successive approximation" training exercises.

The devices of this invention are thus handheld, with the handle protruding from between the lips and the palatal portion loosely fitting against the hard palate. The devices differ from each other by substantial variation in the palatal base portion or in the handle. These variations, called "activators" are designed to help tongue/lip in movements and placements needed to articulate the different consonants /p/, /t/ and /k/, all of which require either strong lip closure or tongue-palate contact.

Referring preliminarily to the drawings, it will be noted that in the series FIGS. 1A-E and 3A-E, the superior surface, tongue, lip and handle surfaces are facing the viewer; whereas in FIGS. 2A-E inclusive the superior portion, namely the tongue surface, is shown on the right portion of each device and the lip and handle portion on the left. The inferior portion of the respective FIGS. 2A-E devices, the palate contacting surface, is on the right hand side, the lip and handle portion being shown to the left, thereof. According to these FIGS. 1A, 2A, 3A concepts, positioner 10 comprises: an elongated palatal base 10 for insertion into the mouth of the person, the base itself defining a convex upper surface to conformably engage the palate of the person's mouth and a concave lower surface 15 forming an artificial tongue contacting surface, an open end of said base terminating in an edge which is normal to a longitudinal centerline of the positioner and a closed end of said base converging into a transversely curvilinear shelf of reduced width, relative to the open end. A handle 12 projects from the closed end of the base, the handle being of less width than the palatal base shaped and arranged with the base for manual manipulation externally of the mouth, whereby the handle, engaged also by the lips, may assist in placement of the positioner relative to the person's palate.

Figure 2A:
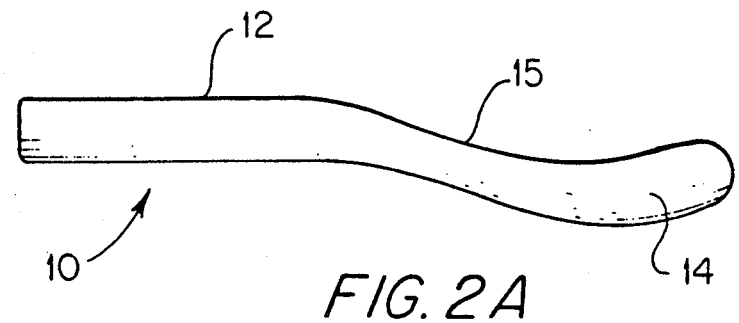
FIGS. 2A, 2B, 2C, 2D and 2E are views in side elevation of the respective devices comprising the kit of the plan views 1A-E inclusive, above. In these drawings the tongue contacting portions are shown at the top right of each figure.
Figure 2B:
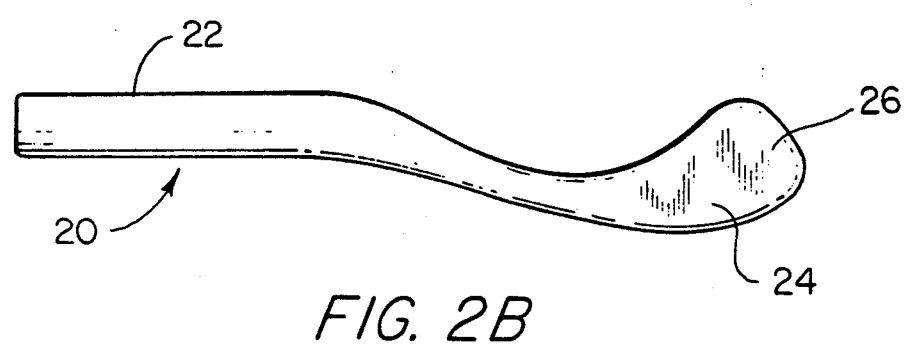

The basic configuration of all the appliances is illustrated in FIGS. 1A, 2A and 3A inclusive. The other four appliances will include added shapes or deletions as will be apparent.

Positioners 10 and 20 are used in connection with one another for exercising the contact of the back of the tongue to the patient's palate. Tongue positioner 10 of FIGS. 1A, 2A and 3A defines a narrow handle 12 which is ¼ inch wide and 2 inches long. The interior portion 15 of the palatal base 14 is a convex surface to provide an easy contact for the tongue. All other devices 20, 30, 40, 50 have a similar convex surface. Between handle and base portions the device of this configuration assists in developing the "back sounds" of speech in use with device 20 by facilitating contact of the back of the tongue with the area defined by the junction of hard and soft palates.

Positioner 20, FIG. 1B is similar to positioner 10, FIG. 1A. It includes handle 22, palatal base 24, quasi-rectangular thickening extension 26 of the palatal base, adding to its length and thickness. The palatal base 24 defines at its open end an activator target ridge below the concave lower surface of the base. This presents an easier target for the patient's back tongue movement.

The two tongue positioners 10 and 20 thus aid in direct movement of the back of the tongue towards contact on the palate, especially at the junction of the hard and soft portions, thereof. This combination aids in production of the linguovelar, or "back sound", /k/-/g/-/ng/ as well as in the swallowing motion. These positioners are especially useful for: stroke patients with limited range of motion of the tongue in rear elevation, post-surgerized hemiglossectomees due to cancer of the tongue, laryngectomees learning esophageal speech where the tongue is needed to make the /k/-/g/-/ng/ sounds for air injection for speech training. Both 10/20 positioners facilitate swallowing by motion exercises.

Figure 2C:
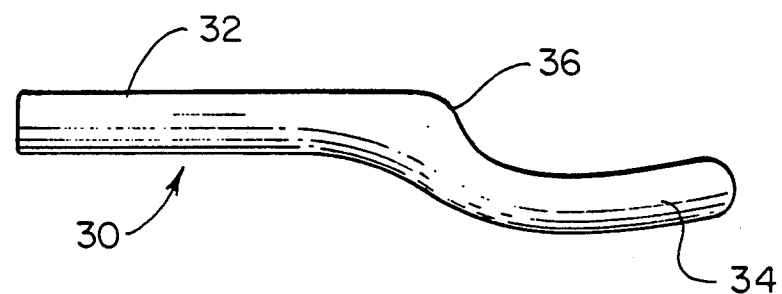

Positioner 30 of FIGS. 1C, 2C and 3C is utilized to strengthen the tongue tip in swallowing initiation as well as in orientation for contacts, to develop the /t/-/d/-/n/ speech "front sound". The handheld handle 32 is narrow, being ¼ inch wide. The front of the palatal base 34 is thickened at 36 for easy contact, and this thick rim or ramp is defined adjacent the closed end to facilitate contact of the front of the tongue with the required area of the palate. This tongue exerciser is primarily useful to: esophageal speakers for air injection; stroke and head trauma patients suffering from dysarthria with poor range of motion in elevation for speech and swallowing; droolers and tongue thrusters. As will be noted hereinafter there is a coactive relationship between positioners 30 and 40 in seeking pronunciation of the /t/-/d/-/n/ sounds.

Figure 2D:
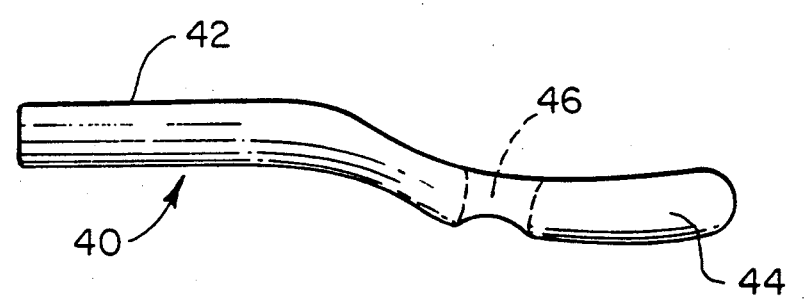

Referring to FIGS 1D, 2D and 3D, the device 40 is used conjointly for front tongue elevation exercise with positioner 30 and for lip exercise it is used conjointly with device 50. The narrow handle thus allows the patient to make contiguous contact of the lips and the hole in the palatal base allows the tongue to provide an exercise for the front of the tongue. As may be apparent, this device 1D, 2D and 3D is used for enhancing speech production of the /t/-/d/-/n/ sounds. The necessary placement of the tip of the tongue is guided by providing a central transversely extending opening adjacent its closed end to expose the front portion of the palate of the mouth. It is ½'inch wide and ¼ inch long.

Figure 2E:
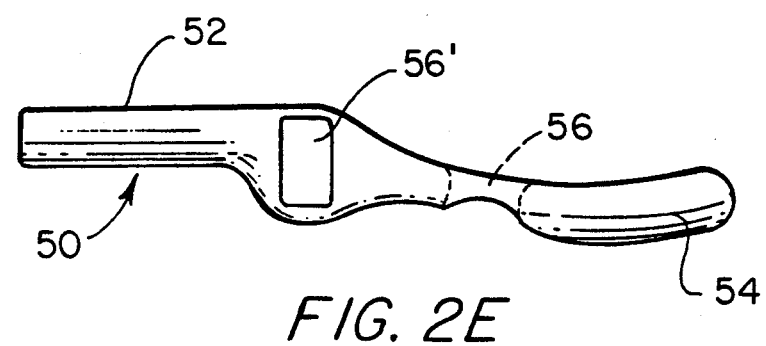

Referring to FIGS. 1E, 2E and 3E, the lip and tongue positioner 50 has a primary handle 52 and an especially wide interconnection 56', 1¼ inches wide and ½ inch thick. A portion of the handle 56+ is the activator to weak lips. The other portion of the handle is to be held. The quasi-rectangular thickness of the handle 56' aids in making an easy closure of the lips and is exercised as such. The palate base 54 has a large target opening 56, ½ inch transversely and ¼ inch longitudinally adjacent its closed end to expose the frontal portion of the palate of the mouth to the tongue of the person. The patient is given instructions to find the opening with the tongue tip, whereby to activate a strong reflex to stretch the tongue to this target. This device aids in developing the bilabial sounds /p/-/b/-/m/.

The two devices 40 and 50 of FIGS. 1D, 2D 3D and 1E, 2E and 3E are employed in sequence for persons who have lip and tongue problems, wherein strong closure of the lips is needed to produce the bilabial sounds, /p/-/b/-/m/. As known, weak lip closure is not only derived from "tongue thrusters" with abnormal habit problems, but also from persons having brain damage, such as stroke victims.

Such brain damaged persons have in many cases both partial lip and partial tongue paralysis Speech and swallowing is therefore affected and generally drooling problems are manifested due to ineffectual closure of the lips and or tongue palate contact. Esophageal speakers must make a firm lip closure as well as tongue tip—palate closure to inject air needed for esphageal speech; thus these FIGS. 1D, 2D, 3D; 1E, 2E, 3E devices apply.

Summarizing, all of the appliances have basic commonalty of narrow handle and hard palatal contact portions. Nonetheless, variations in configuration prevail as between the modifications depicted in the aforesaid figures, as follows. All of the devices as a set are exercisers for oral musculature affecting some aspects of speech and swallowing The FIGS. 1A-1B devices will be used coactively to aid in the retroflexing of the tongue for the /k/-/g/-/ng/ sounds and swallowing movement The FIGS. 1C-1D devices are used coactively to exercise the elevation of the front of the tongue for the speech sounds /t/-/d/-/n/ and for swallowing movement The FIGS. 1D and 1E devices are used coactively for strengthening lip closure and reversing tongue thrusting; the /p/-/b/-/m/ sounds are enhanced thereby Initiating swallowing movements are likewise enhanced through exercise thereby The basic configuration is shown in FIGS. 1A, 2A, 3A and the related positioners, which have activator elements designated numerically as 26, 36, 46, 56, and 56'.

I claim:

1. A prosthetic plural positioner training kit for orally handicapped persons, each positioner thereof comprising in commonalty:
   (a) an elongated palatal base for insertion into the mouth (of a user) said base defining a convex upper surface to conformably engage the palate of the mouth and a concave lower surface forming an artificial tongue contacting surface, an open end of said base terminating in an edge which is normal to a longitudinal center line of the positioner and a closed end of said base converging into a transversely curvilinear shelf of reduced width relative to the open end;
   (b) a rigid handle projecting from the closed end of the base, said handle being of less width than the palatal base, shaped and arranged with the base for manual manipulation externally of the mouth, whereby the handle, engaged also by the lips, may assist in placement of the positioner relative to the person's palate.

2. The positioner according to claim 3 wherein at the closed end of the base, the handle is enlarged, thickened transversely and shaped to be straddled by the user's lips, said palatal base defining an enlarged transversely extending central opening, adjacent its closed end to expose the frontal portion of the palate of the mouth to the tongue of the user.

3. The positioner of claim 1, said palatal base defining a central transversely extending opening, adjacent its closed end to expose the front portion of the palate of the mouth for exercising the front of the user's tongue.

4. The positioner according to claim 1, wherein the rim front of the palatal base, adjacent to the closed end of the base is of increased thickness, relative to comparable other side portions of said palatal base whereby to provide a target ramp for the tip of the user's tongue.

5. The positioner according to claim 1, wherein said palatal base defines extended elongation along its axis and between ends to engage an extended portion of the user's hard palate, said palatal base further defining at its open end an activator target ridge which extends below the concave lower surface of the palatal base into the person's oral cavity, opposite the user's tongue.

* * * * *